(12) United States Patent
Findlay et al.

(10) Patent No.: US 10,835,171 B2
(45) Date of Patent: Nov. 17, 2020

(54) INGESTION MONITORING SYSTEMS

(71) Applicant: BUDDI LIMITED, Rickmansworth (GB)

(72) Inventors: Ewan Findlay, Milnathort (GB); Sara Murray, Rickmansworth (GB)

(73) Assignee: BUDDI LIMITED, Rickmansworth (GB)

( * ) Notice: Subject to any disclaimer, the term of this patent is extended or adjusted under 35 U.S.C. 154(b) by 492 days.

(21) Appl. No.: 15/542,647

(22) PCT Filed: Jan. 13, 2016

(86) PCT No.: PCT/GB2016/050077
§ 371 (c)(1),
(2) Date: Jul. 10, 2017

(87) PCT Pub. No.: WO2016/113562
PCT Pub. Date: Jul. 21, 2016

(65) Prior Publication Data
US 2017/0367639 A1     Dec. 28, 2017

(30) Foreign Application Priority Data

Jan. 15, 2015   (GB) .................................. 1500648.9

(51) Int. Cl.
*A61B 5/00* (2006.01)
*A61B 5/11* (2006.01)
(Continued)

(52) U.S. Cl.
CPC .......... *A61B 5/4205* (2013.01); *A61B 5/0002* (2013.01); *A61B 5/02055* (2013.01); *A61B 5/11* (2013.01); *A61B 5/6804* (2013.01); *A61B 5/72* (2013.01); *A61B 5/7225* (2013.01); *A61B 5/7257* (2013.01); *A61B 5/01* (2013.01); *A61B 5/024* (2013.01); *A61B 5/02416* (2013.01); *A61B 5/1455* (2013.01);
(Continued)

(58) Field of Classification Search
None
See application file for complete search history.

(56) References Cited

U.S. PATENT DOCUMENTS 6,173,074 B1   1/2001   Russo
6,570,500 B1   5/2003   Pieper
(Continued)

FOREIGN PATENT DOCUMENTS

| JP | 2005304890 | 11/2005 |
|---|---|---|
| WO | WO 2008/157622 | 12/2008 |
| WO | WO 2014/159749 | 10/2014 |

OTHER PUBLICATIONS

Search Report from related GB Application No. 1500648.9 dated Jul. 9, 2015.
(Continued)

*Primary Examiner* — Michael W Kahelin
*Assistant Examiner* — Shirley X Jian
(74) *Attorney, Agent, or Firm* — Haynes and Boone, LLP

(57) ABSTRACT

An ingestion monitoring system (100) comprising: one or more acoustic transducers (102); an analogue to digital converter (208) arranged to convert electrical signals from the acoustic transducer to digital form; and a processor (210) arranged to process the digital signal to detect an ingestion event.

18 Claims, 7 Drawing Sheets

(51) Int. Cl.
*A61B 5/0205* (2006.01)
*A61B 5/01* (2006.01)
*A61B 5/1455* (2006.01)
*A61B 5/024* (2006.01)

(52) U.S. Cl.
CPC .......... *A61B 5/6801* (2013.01); *A61B 5/6813* (2013.01); *A61B 2562/0204* (2013.01)

(56) References Cited

U.S. PATENT DOCUMENTS

| | | | |
|---|---|---|---|
| 9,198,621 B2* | 12/2015 | Fernstrom | A61B 5/1112 |
| 10,143,420 B2* | 12/2018 | Contant | A47G 21/02 |
| 2003/0152607 A1 | 8/2003 | Mault | |
| 2005/0105644 A1 | 5/2005 | Baxter et al. | |
| 2008/0264180 A1 | 10/2008 | Gakhar et al. | |
| 2009/0012433 A1* | 1/2009 | Fernstrom | A61B 5/1112 |
| | | | 600/593 |
| 2011/0125063 A1* | 5/2011 | Shalon | A61B 5/0006 |
| | | | 600/590 |
| 2011/0276312 A1 | 11/2011 | Shalon et al. | |
| 2013/0336519 A1* | 12/2013 | Connor | G06K 9/00771 |
| | | | 382/100 |
| 2014/0081578 A1* | 3/2014 | Connor | G06F 19/3475 |
| | | | 702/19 |
| 2014/0349256 A1* | 11/2014 | Connor | G09B 19/0092 |
| | | | 434/127 |
| 2014/0349257 A1* | 11/2014 | Connor | G09B 19/0092 |
| | | | 434/127 |
| 2014/0350353 A1* | 11/2014 | Connor | A61B 5/4866 |
| | | | 600/301 |
| 2017/0150930 A1* | 6/2017 | Shikii | A61B 5/0261 |

OTHER PUBLICATIONS

PE Williams & MW Hoffman, Classification of military ground vehicles using time domain harmonic amplitudes, IEEE Trans Inst & Meas 60(11) 2011, pp. 3720-3731, doi 10.1109/TIM.2011.2135110.

A Alkilani & A Shirkhodaie, A survey of acoustic signature recognition & classification techniques for persistent surveillance systems, Proc SPIE vol. 8392 83920U-1, doi 10.1117/12919872.

DG Childers et al., Cepstrum—A guide to processing, Proc IEEE 65(10) 1977 pp. 1428-1443.

T Kinnunen, H Li, An overview of text-independent speaker recognition: From features to supervectors, Speech Communication vol. 52(1), Jan. 2010 pp. 12-40, DOI: 10.1016/j.specom.2009.08.009.

* cited by examiner

INGESTION MONITORING SYSTEMS

CROSS-REFERENCE TO RELATED APPLICATIONS

This application is a U.S. national stage continuation application under 35 U.S.C. § 371 of International Patent Application No. PCT/GB2016/050077 filed on Jan. 13, 2016, which claims the benefit of Great Britain Patent Application No. 1500648.9 filed on Jan. 15, 2015, the contents of each of which are incorporated herein by reference.

TECHNICAL FIELD

The present disclosure relates to an ingestion monitoring system.

BACKGROUND

Increasing obesity has driven concern that people eat either too much, too often or at the wrong times, thereby damaging their own health. When monitoring food and drink consumption, there may be a large disparity between what people think they eat and what they actually eat. Although it is well understood that there is a relationship between diet, exercise and obesity, real data concerning the factors most contributing to changing outcomes is not available.

To this end, there are now mobile phone applications, where users either take photographs of their meals or keep food diaries and the phone application calculates an approximate number of calories along with approximate proportions of fat, protein and carbohydrates. This data can be combined with activity data from the phone or an additional wearable activity monitor.

Another approach proposed is to use near infrared (NIR) spectroscopic data from meals and generate a content profile. This has the potential to inform on the content, and possibly the volume, of food to be consumed.

In all the proposed devices to date, the potential for the users to lie to themselves is high and manual input effort is required to provide complete data. This creates an inconvenience factor: taking out a camera or other device to "scan" your food takes time and effort.

Simultaneously, increasing alcoholism and alcohol-related crime is encouraging the use of monitoring of alcohol intake by individuals. Current body-worn systems have inherent problems which make them expensive and require data analysis by experts to determine whether alcohol was consumed.

In all the current diet aiding technology there is the potential for under-estimation of calorie intake through user self-deception. Use of a content scanning device or a photograph-based system requires an iron determination to scan each food item, and it is tempting to omit scanning items with high calorific value such as cream-cakes, chocolate or a second glass of wine. Users therefore find it hard to keep accurate records, and are tempted to make records that give a false impression of their true consumption.

The majority of the existing systems are optical and, thus, will require a line of sight to the food and active deployment by the user.

Therefore, there is a need for improved systems for the monitoring of eating and drinking behaviour. Improved systems should be easy to use and provide accurate results.

SUMMARY OF THE DISCLOSURE

According to a first aspect of the disclosure there is provided an ingestion monitoring system comprising:

one or more acoustic transducers;

an analogue to digital converter arranged to convert electrical signals from the acoustic transducer to digital form; and a processor arranged to process the digital signal to detect an ingestion event.

Optionally, the system comprises a filter for filtering out high-frequency noise prior to analogue to digital conversion and/or processing.

Optionally, the system comprises one or more other types of sensors which provide ancillary data for correlation with acoustic signals.

Optionally, one sample from each of the sensor types is considered as a vector and an event is a time evolution of that vector.

Optionally, raw signals generated by the sensors are transformed into a parameter space where the axes of the parameter space coincide with indicators for given actions.

Optionally, thresholding is applied directly to the indicators, whereby an action is deemed to have occurred if its threshold is exceeded.

Optionally, low frequency components are observed after low pass filtering and high frequency components are observed by transformation into a frequency domain over a sampling window.

Optionally, transformation into a frequency domain comprises a short term Fourier transform.

Optionally, the system comprises a statistically derived model which assigns probable causes to signal events and over a series of events infers an activity that is taking place.

Optionally, the system comprises a signal classification model used to classify detected signals from the acoustic transducer(s) and any other sensor types.

Optionally, the signal classification model employs a Gaussian Mixture Model technique, a Hidden Markov Model technique, or a hybrid technique employing both Gaussian Mixture Model and Hidden Markov Model techniques.

Optionally, one or more of the acoustic transducers comprises a housing portion that contacts the skin of the user and a diaphragm portion that is held above the skin so that it picks up vibrations in an isolated volume of air at the skin.

Optionally, the system comprises a first acoustic transducer for placing at the skin of a user being monitored and a second acoustic transducer for placing in a position where it receives airborne vibrations.

Optionally, the system comprises a motion sensor.

Optionally, movement detected by the motion sensor is identified as a pattern which correlates with a given action.

Optionally, the movement is classified as being vigorous, minimal, or still.

Optionally, the motion sensor is arranged to detect arm motions indicative of cutlery use or eating by hand.

Optionally, the system comprises a heart rate monitor.

Optionally, the system comprises a photoplethysmographic sensor.

Optionally, the photoplethysmographic sensor is arranged to detect a period of apnoea related to a swallowing event.

Optionally, a swallowing event is detected if a period of apnoea is correlated with an acoustic swallowing signature from airborne or intra-body vibrations.

Optionally, a volume of ingested matter is estimated based on the detection of a swallowing event together with a pharyngeal volume.

Optionally, the pharyngeal volume is derived from a user's height and optionally additionally from their weight.

Optionally, the system comprises a temperature sensor.

Optionally, a combination of heart rate sensor, motion sensor and photoplethysmographic sensor are provided; and consumption of alcohol is inferred if there is an increase in heart rate and blood profusion in subcutaneous blood vessels without a corresponding motion that correlates to exercise, including that of cutlery use or eating by hand.

Optionally, the system comprises a satellite navigation system receiver.

Optionally, the acoustic transducer senses airborne sounds and vibrations transmitted through a body.

Alternatively, the system comprises a first acoustic transducer for sensing airborne sounds and a second acoustic transducer for sensing vibrations transmitted through a body.

The output from each of the acoustic transducers is provided to an analogue to digital converter, which may be provided in common for use by each, all or some of the transducers, or a plurality of analogue to digital converters may be provided, one for each transducer.

Optionally, the airborne vibrations and the vibrations transmitted through a body are correlated and combined to form part of a signature relating to an event.

Optionally, the system comprises a wearable device.

Optionally, the wearable device comprises a wristband, a necklace, an anklet, or an ear hook.

Optionally, the system comprises a portable computing device.

Optionally, the system comprises one or more fixed location acoustic transducers.

Optionally, the system comprises two or more of: a wearable device, a portable computing device, and one or more fixed location acoustic transducers.

Optionally, the system comprises a wearable device that comprises the acoustic transducer, and a portable computing device that comprises other types of sensors which provide ancillary data for correlation with acoustic signals.

Optionally, the system comprises one or more fixed location acoustic transducers and a portable computing device, and sounds are identified as originating from one particular user based on the proximity of the portable computing device to one or more of the transducers.

Optionally, a device housing the acoustic transducers and any other sensors comprises a communication means for transmitting sensor data to a remote location for identification.

Optionally, a device housing the acoustic transducers and any other sensors also comprises the filter and analogue to digital converter.

Optionally, identification at the remote location comprises a server running a statistically derived model or signal classification model.

Optionally, the server receives data from multiple devices and uses the combined data to improve the models used for identification.

According to a second aspect of the disclosure there is provided a method of monitoring ingestion, comprising detecting with a transducer an acoustic vibration caused by an ingestion event, converting the electrical signals from the transducer to digital form; and processing the digital signal to detect an ingestion event.

A method according to the disclosure also comprise providing and using the features of the systems of the first aspect and as described elsewhere herein.

According to a third aspect of the disclosure there is provided a computer program product, that when run on a computer, processes a received digital signal to detect an ingestion event.

Optionally, the computer program product is provided as an application which can be installed on a portable computing device.

The computer program product may implement the methods/systems of the first two aspects and as described elsewhere herein.

According to a fourth aspect of the disclosure there is provided a wearable device comprising an acoustic transducer, an analogue to digital converter arranged to convert electrical signals from the acoustic transducer to digital form, and a communication means for sending the digital signals to a remote location for processing to detect an ingestion event.

The wearable device may comprise various other features of the system of the first aspect, and as described elsewhere herein.

According to a fifth aspect of the disclosure there is provided an ingestion monitoring system comprising one or more acoustic transducers which are arranged to sense airborne sounds and vibrations transmitted through a body.

The system of the fifth aspect may comprise various other features of the system of the first aspect, and as described elsewhere herein.

The computer program product may be stored on or transmitted as one or more instructions or code on a computer-readable medium. Computer-readable media includes both computer storage media and communication media including any medium that facilitates transfer of a computer program from one place to another. A storage media may be any available media that can be accessed by a computer. By way of example such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fibre optic cable, twisted pair, digital subscriber line (DSL), or wireless technologies such as infra-red, radio, and microwave, then the coaxial cable, fibre optic cable, twisted pair, DSL, or wireless technologies such as infra-red, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The instructions or code associated with a computer-readable medium of the computer program product may be executed by a computer, e.g., by one or more processors, such as one or more digital signal processors (DSPs), general purpose microprocessors, ASICs, FPGAs, or other equivalent integrated or discrete logic circuitry.

BRIEF DESCRIPTION OF THE DRAWINGS

The disclosure will be described below, by way of example only, with reference to the accompanying drawings, in which.

DETAILED DESCRIPTION

Figure 1:
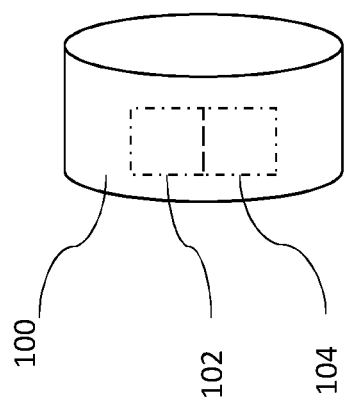
FIG. 1 shows a wristband, for use in a first embodiment of an ingestion detection system.

The present disclosure relates to systems and devices for acoustic monitoring of a person to detect eating and/or drinking activities. There are various "ingestion events" that can be detected by the disclosure in the various embodiments which are explained below, including intake of food or drink into the mouth cavity, mastication of food, and swallowing of food or drink. Each of these events can have their own sub-classes of more specific events; for example, the acoustic signature of mastication of food may be classed as a crackling "crunching" sound or a smoother "munching" sound and thus provide some basic discrimination food type being eaten.

The system may in optional embodiments also comprises sensors of other types besides acoustic monitors which provide ancillary data. This ancillary data can be used for the detection or inference of various other events, actions, or conditions of the environment or a user being monitored. The other types of sensors that may be used may include, without limitation, one or more of: accelerometers or other motion sensors, heart rate monitors, respiration monitors, temperature sensors, and global navigation satellite system receivers.

In embodiments which have a plurality of sensor types, the system may switch between a low power mode where a subset of sensor types are operative, ideally a single sensor type; and an operative mode where all the sensor types or a larger subset of them are operative.

The sensor type(s) operative in the low power mode can be used to detect an event which can then be used to wake up the other sensor types for ingestion detection. For example, the acoustic sensor and/or a motion sensor could detect an event of interest and then awaken the other sensors. It is also possible that one or more specific types of sensor are disabled in the system's operative status depending on an inferred context.

In both modes the data from the sensors can be considered as being simultaneous even if the sensors of different types are read out sequentially. The sample period can be less than 2000 Hz without losing any relevant information from the sensors, so the inherent sampling delay will have minimal effect on event identification.

Preferably, after amplification and filtering to remove high frequency noise, the signals from the sensor(s) are digitised to allow use of digital signal processing techniques to be employed. The signal profile for an ingestion event or other type of event can cover a number of sampling periods and be present on a plurality of sensors.

The provision of one or more additional sensor types in addition to an acoustic sensor, and the combination of the sensor(s) readouts with the acoustic data helps verify through inference the detection of an ingestion event. Inference of an event may use any appropriate statistical inference method such as Bayesian inference. It will be appreciated that other inferential paradigms may be used if desired.

A single sample of the set of sensors can be considered as a vector and a single ingestion event (such as food mastication) can be considered as the time evolution of that vector. The time evolution of the vector containing all sensor data can be treated in a number of ways. One preferred treatment is where low frequency components and single events are observed after low pass filtering and high frequency components are observed by taking a short term Fourier transform of limited sampling windows. The consequent array of data will also evolve in time; for instance identification of a mastication signal followed by a swallow signal would indicate eating.

To identify the events, actions or conditions which can be inferred from the ancillary data that is given by multiple sensor types, the time evolving data can be input to a statistically derived model which assigns probable causes to signal events and over a series of events infers the overall condition or activity taking place.

The degree of accuracy required along each axis in parameter space depends on the context. For instance, movement as measured by an accelerometer can be identified as a pattern which correlates with the given action, running say, or categorised as vigorous movement as opposed to minimal movement or being still. The same approaches can be applied to all sensor signals.

If the raw signals generated by the sensors are transformed into a parameter space where the axes coincide with the indicators for given actions, thresholding can be directly applied to the indicators to imply the action has occurred. Such transforms can be derived empirically using statistical techniques.

Examples of pre-processing techniques we consider applicable, other than those mentioned above, include cepstrum decomposition, frequency binning using a filter series and wavelet analysis. Signals can be treated using a plurality of different techniques even if they originate from the same sensor. Pre-processing can be regarded as a transform process acting on the raw sensor signals. The pre-processed data can be input to a signal classification model derived from reference data and a class identified.

There are a number of statistical techniques for building classification models which we consider as useful. The use of Gaussian mixture models allows us to identify clusters of correlated events in the data set and distinguish two or more event types happening simultaneously. An output model based on Gaussian mixtures would give a likelihood for the event(s) observed belonging to a certain class(es). On the other hand hidden Markov models can be used to identify patterns in sequential data. Here the previous observation is taken into account when establishing the likelihood of the current observation. A hybrid technique could be used, employing both GMM and HMM models. They could be run in parallel or run selectively to test for different events. In all cases the likelihood of the observation being of a certain type can be subject to a thresholding process, either soft or hard.

The system can be implemented in a variety of different physical implementations and layouts. In some embodiments, the system may comprise a wearable device, which comprises an acoustic transducer. In these embodiments, the acoustic transducer of the wearable device can be placed close to or in contact with the skin so that it can pick up vibrations that are transmitted through the body of a user being monitored. It may also be able to pick up sound vibrations that are transmitted through the air. The wearable device may also comprise other sensors, which as mentioned above can record ancillary data for inferring ingestion and other events.

The wearable device can take any suitable form, but for example may comprise a wristband (to be worn around a user's wrist); an anklet (to be worn around a user's ankle), an ear hook (to be worn around a user's auricle), or a necklace (to be worn around a user's neck).

In other embodiments, a wearable device is not provided and one or more acoustic transducers are provided at fixed locations, for example in a kitchen or dining room. These transducers can provide data to a processor as described above for the detection of an ingestion event. The presence of other sensors is not essential. The transducers are "fixed" in the sense that they will normally be stationary while a user is eating and are not worn or carried by the user. However they may be repositioned from time to time as required.

In other environments, some or all of the ingestion monitoring system is provided as an application which can be run by a smartphone, tablet or other computing device. The application may make use of existing device microphones and/or other sensors; or the device may be provided with customised sensors for performing the methods of the disclosure.

Hybrid embodiments are also possible, using any combination of two or more of a wearable device, one or more fixed transducers, and a (portable) computing device running a suitable application. For example, acoustic detection could be provided by either a wearable device or by one or more fixed transducers, and ancillary data for inference of ingestion or other events could be provided by a smartphone. Or, acoustic detection could be provided by a combination of a wearable device arranged to detect vibrations through a user's body and a set of fixed transducers arranged to detect sound transmitted through the air. Also, it is possible to provide two or more wearable devices for redundancy or for gathering different types of data.

There are also various ways to implement the network architecture of the system and it will be appreciated that the present disclosure is not limited to any particular physical or logical architecture. At one extreme, a wearable device, portable computing device, or fixed transducer housing will be provided with all the necessary components for carrying out the detection of ingestion and other events. However it will normally be preferred to carry out one or more processing tasks remotely from the sensors, optionally at a remote server via an internet connection. The processing (in whole or in part) could also be carried out by a portable computing device such as a smart phone. The portable computing device may be in communication with a remove server. This technique allows the bill of materials for a wearable device to be minimised. Also, if data is collected centrally from multiple devices or multiple users it can be combined to continuously improve statistical models and inference engines used in the detection and inference of events.

As mentioned above, a wearable device which may be provided as part of some preferred embodiments, may comprise a wristband, necklace, anklet or ear hook. Along with an acoustic sensor, additional sensors may be included which may comprise without limitation one or more of: a motion sensor to detect and identify physical activity; a heart rate sensor, possibly using optical detection; a respiration monitor, a temperature sensor, which can compare the temperature of the skin to the ambient temperature; and a global satellite navigation system receiver, which can identify user location.

The acoustic sensor may be capable of detecting both vibrations transmitted through the body and through the air to the wearable device, and may have a suitably high dynamic range to enable this. To aid in the detection of vibrations from the body, the acoustic transducer comprises a portion that faces the skin of a user that is being monitored. It may touch the skin or be positioned close to the skin. It may still be used if one or more layers of clothes are worn between the skin and the transducer. The part of the acoustic transducer that faces the skin can be impedance matched to optimise the coupling of sound to the acoustic transducer(s). Also the acoustic transducer(s) can be mounted such that airborne sounds will be detected to a sufficient degree.

An acoustic sensor according to one embodiment comprises a housing portion that contacts the skin of the user (optionally via one or more layers of clothing), and has a diaphragm portion that is held above the skin so that it picks up vibrations in an isolated volume of air at the skin.

In a preferred embodiment, the system comprises at least two acoustic transducers; one being of the type mentioned above which is coupled to the skin via a housing with an isolated mobile volume of air; and the other with a housing isolated from the skin and a diaphragm coupled to the air.

The low frequency body-transmitted vibrations and the higher frequency airborne acoustic vibrations are temporally correlated and the combination of the two can form a signature relating to an event. This may require filtering and transformation to extract frequency information, suitably by a short term Fourier Transform. The signature thus derived can be considered as a pattern of values in parameter space, derived either from a single sensor or from multiple sensors.

A wearable device may also advantageously be provided with a photoplethesmographic sensor which may operate as a heart rate sensor or a respiration monitor. It may also be used to detect short term apnoea caused by swallowing; and this can be correlated with the detection of vibrations by an acoustic transducer. When looked at from the anatomical view point a swallowing event is due to a series of muscle movements. We are interested in the pharyngeal phase of swallowing, which sees food being sent backwards into the pharynx and the temporarily closes the larynx preventing breathing along with other entrances to the pharynx. Note, the sensation of hearing oneself swallow comes primarily from closure of the nasopharynx and the consequent opening of the auditory tube, which acts to equalise the pressure between the nose and the inside of the ear-drum. In the present system we can detect the period of apnoea related to swallowing via a photoplethesmographic sensor mounted on or close to the skin, and optionally in addition the translated/related small movements/vibrations related to the muscle movements.

For instance the action of swallowing can be observed as a low frequency (<100 Hz) vibration in the body and as a perturbation to the breathing related modulation of the transcutaneous photoplethysmographic heart rate signal. This can be distinguished from a cough, say, by the observation of the differences in frequency content as seen in a discrete Fourier transform and how it is manifest in the heart rate signal. Another example where the signal presents itself in different domains is the mastication of food; again there will be a low frequency signal transmitted through the body to the device and an audible sound transmitted through the atmosphere to the device. Differentiation of the wearer's mastication from that of his neighbour can be done on the presence of the low frequency body-transmitted part of the acoustic "mastication signal."

Swallowing can also be detected from acoustic signals alone, without the system requiring a photoplethesmographic sensor. A photoplethesmographic sensor will normally provide a clearer swallowing signal but it may be preferred to be omitted for reasons of cost (lower bill of materials); or it may not be needed if the acoustic signals are to be combined with other types of sensor data in an inference engine.

Another aspect of the disclosure relating to swallowing detection is an inferred quantification of the amount of food consumed. Ideally we want to know the size of the user's pharynx to estimate the average amount of food swallowed in a single event.

However, this cannot be obtained easily and we use an estimate in its place to in turn give an estimate of the average amount of food ingested in a single swallow. An estimate of pharyngeal volume and therefore the average volume of food swallowed can be obtained from a person's height, optionally in combination with their weight.

The system can therefore passively estimate calorific intake by using inference gathered from a number of sensors, including an acoustic sensor, a motion sensor and a photoplethasmographic heart rate sensor. It does this by inferring the type of food swallowed from the noises of mastication and incidental noises related to eating and drinking and the volume from the swallowing frequency.

The effect of the ingested food and drink may be also be inferred from the affects it has on the device wearer's actions and physiological state. For instance if excessive amounts of alcohol are imbibed the wearer may become unsteady on their feet and their skin temperature will rise with respect to the ambient temperature.

Various specific embodiments of the disclosure will now be explained. FIG. 1 shows a wristband 100 which comprises an embedded microphone 102 and other circuitry 104 comprising amplification, control and communication circuitry. The communication circuitry may be of any suitable type, such as ANT or ANT+, Bluetooth or other radiofrequency circuitry. The wristband may also contain motion sensors (including accelerometers and/or gyroscopes) along with devices aimed at generating other biometric data that can be correlated with the acoustic signatures.

When the user eats or drinks, the low frequency vibrations associated with chewing and swallowing are transmitted through the body to the wristband 100. These vibrations will be accompanied by airborne sounds, also indicative of eating or drinking. The wristband 100 is devised such that its housing couples sound transmitted along the radius and ulna and evident on at the skin surface to the microphone 102, which converts the vibration into its electrical analogue; the acoustic signal. The acoustic signal is then filtered to remove sounds other than those at the frequency of interest and digitised prior to further filtering and a pre-processing step before being sent for signature recognition. Signature recognition may occur inside the wristband, or may be passed to software in either a separate mobile device or a remote server.

The vibrations transmitted through the body and through the air will arrive at the device within two milliseconds of each other. These two components will overlap temporally and in frequency space; thus effectively being mixed at the detector/microphone. However, they can be recognised separately in a combined parameter space and separated after coordinate transforms in that space. The nature of the parameter space and coordinate transform may be determined using statistical techniques.

Figure 2:
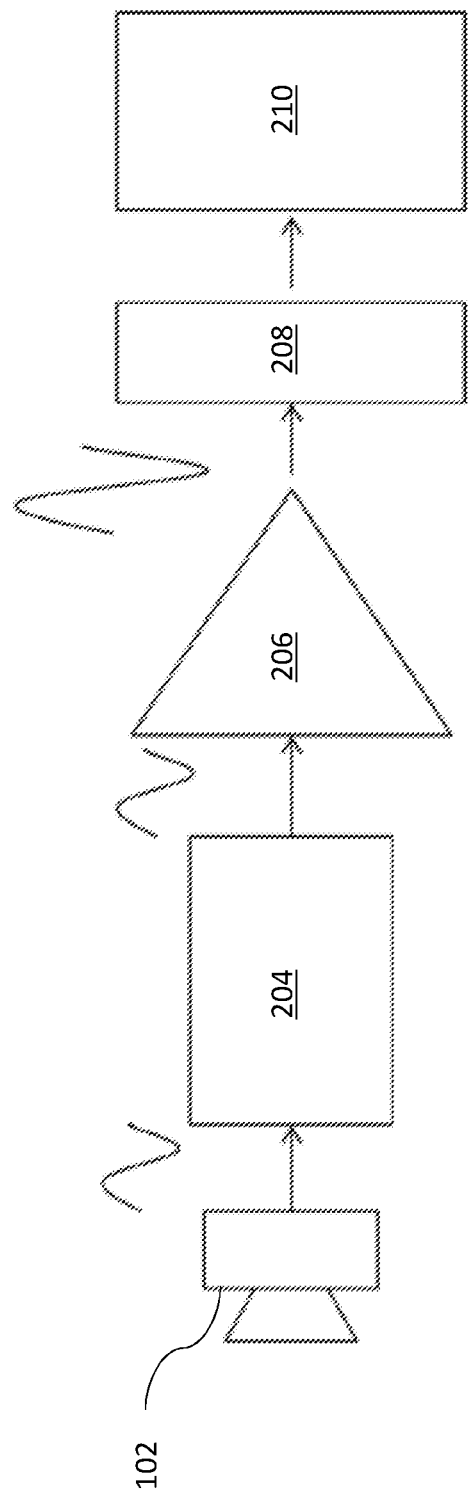
FIG. 2 shows an example detection system which may be incorporated within the wristband of FIG. 1 and in other embodiments.

FIG. 2 shows an example detection system which may be incorporated within the wristband 100. A MEMS microphone 102 provides an output to a processing chain 204-210, which collectively form the other circuitry 104 shown in FIG. 1. Here, the processing chain comprises a preliminary analogue filtering stage 204, amplifier 206, analogue to digital converter (ADC) 208 and processor 210. These components remove high frequency noise and any DC level from the signal prior to digitisation.

Figure 9:
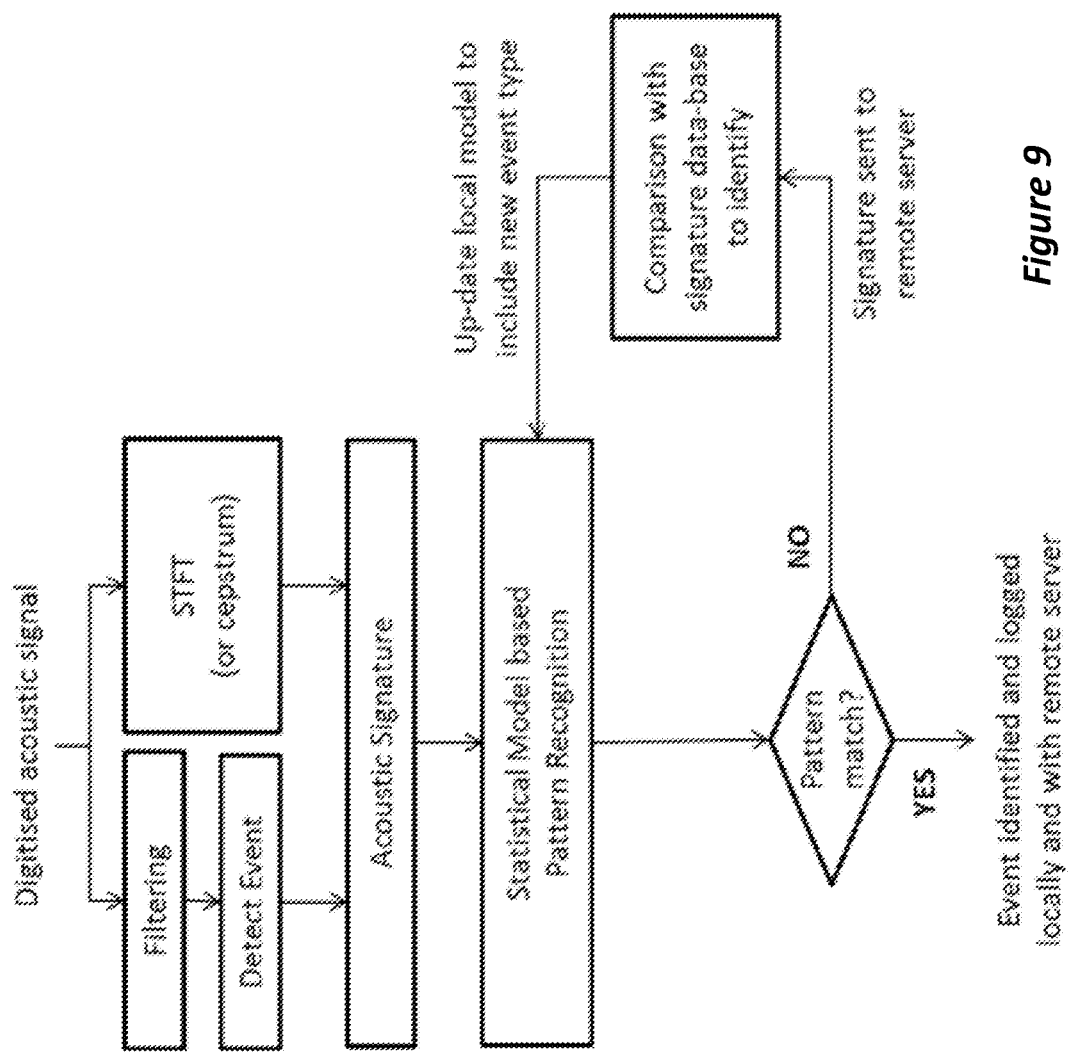
FIG. 9 illustrates signal processing techniques applicable to the present disclosure.

The processor may comprise components which are illustrated in FIG. 9; a bandpass filter implemented in the digital domain coupled to a windowing function such as a hamming window; a transform into the frequency such as a short term Fourier transform, or a cepstrum analysis step; and a parametric comparison using statistical pattern recognition techniques such as Gaussian mixture models and Hidden Markov models to identify the acoustic signature. Ideally such a process can be personalised by further application of statistical techniques to give a higher accuracy in the identification of eating or drinking actions.

Figure 3:
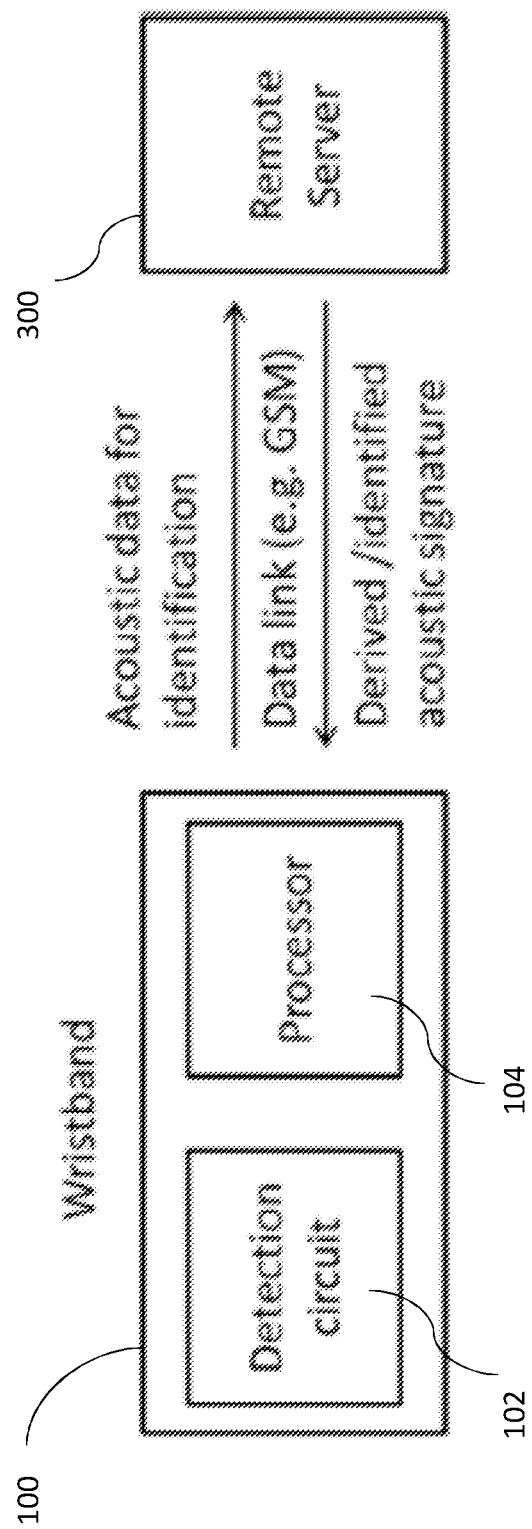
FIG. 3 shows the functional interaction of a wearable or non-wearable device housing an acoustic transducer with a remote server.

FIG. 3 shows the functional interaction of the wristband 100 (or other wearable or non-wearable device housing an acoustic transducer) and a remote server 300. The circuitry 104 (via processor 210) sends acoustic data for identification to the server 300 over a data link, which may suitably be a GSM connection; and may optionally receive a derived/identified acoustic signature back from the server 300 (the return of a signature to the wristband can be omitted in embodiments where the signature is sent to some other device for further processing).

The signal processing chain of FIG. 2 can identify the acoustic signatures of eating and drinking directly, both through their infra-sound and audible content. However, it can also contextualise them with the sounds of cutlery, crockery and glass wear being used, or alternatively other environmental sounds such as those common in fast food outlets. Given that our wristband can house an accelerometer and a heart rate monitor, signals from then can also be correlated with acoustic signatures. These motions might include those involved in using cutlery or raising objects towards the mouth. However, a hand raised towards the mouth does not always indicate eating; and the arm on which the wristband is worn may not be the same as the one which is used for eating. Therefore such a motion can only be taken as indicative of an ingestion event rather than conclusive evidence of it.

Likewise where a photoplethysmographic sensor is provided we may infer swallowing from the data generated by a heart rate monitor using variation in amplitude of the photoplethysmogram related to breathing, as breathing is temporarily halted when swallowing. Other signs of eating and drinking can be found in the patterns generated between a photoplethysmographic signal, motion and eating. These include an increased heart rate without accompanying motion due to digestion and increased blood profusion in subcutaneous blood vessels on imbibing alcohol. Drinking can be distinguished from eating because only one hand is used to hold a glass, as compared with two hands being used for eating.

When the wristband also contains motion sensors, larger body movements can be identified using digital signal processing and correlated with identified eating/drinking actions to give context. At the simplest level, if the user is sitting with only the hands moving this may indicate eating. Alternatively if the user is running it is highly unlikely that they will be eating and the microphone can be turned off or its output ignored. Such power saving applications may be employed to prevent full analysis being performed on sounds generated by normal body movements that will be found not to contain eating related acoustic signatures.

Figure 4:
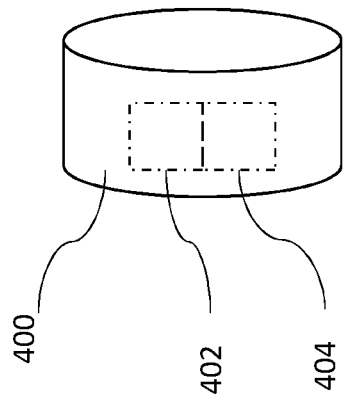
FIG. 4 shows an ear hook, for use in a second embodiment of an ingestion detection system.

A second embodiment is illustrated in FIG. 4, which shows an ear hook device 400 which comprises an embedded microphone 402 and other circuitry 404 comprising amplification, control and communication circuitry. The structure and operation of the ear hook embodiment is generally the same as that discussed above with reference to FIGS. 1 to 3 for the wristband embodiment.

Figure 5:
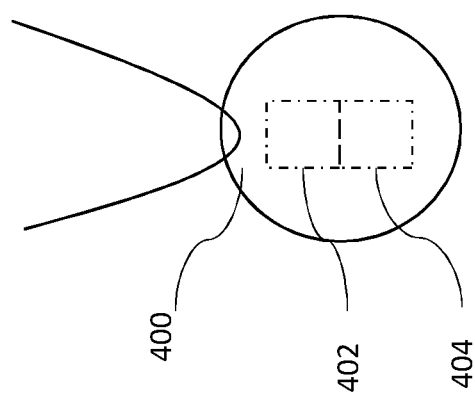
FIG. 5 shows a necklace, for use in a third embodiment of an ingestion detection system.

A third embodiment is illustrated in FIG. 5, which shows a necklace device comprising a pendant 500 which comprises an embedded microphone 502 and other circuitry 504 comprising amplification, control and communication circuitry. The structure and operation of necklace embodiment is generally the same as that discussed above with reference to FIGS. 1 to 3 for the wristband embodiment.

Figure 6:
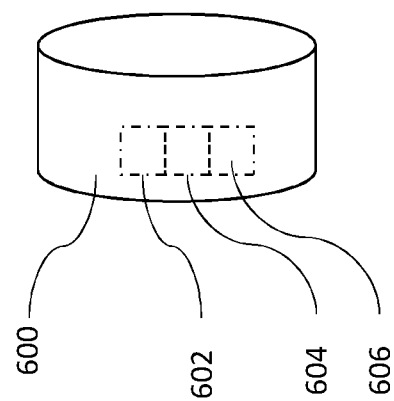
FIG. 6 shows an anklet, for use in a fourth embodiment of an ingestion detection system.

A fourth embodiment is illustrated in FIG. 6, which shows an anklet 600 which comprises an embedded microphone 602 and other circuitry 604 comprising amplification, control and communication circuitry. The structure and operation of the anklet embodiment is generally the same as that discussed above with reference to FIGS. 1 to 3 for the wristband embodiment.

The ankle band 600 may also contain tracking circuitry 606 comprising one or more of a global positioning satellite (GPS) receiver, a motion sensor and a means of communicating such as a radio frequency transceiver, ideally a GSM transceiver.

Here as the distance from the device to the mouth is greater we cannot expect to receive vibrations transmitted through the body and estimates of ingested volume cannot be easily made. However, sounds related to context can be detected. Thus the sounds associated with establishments where alcohol is served can be identified as well as the sounds of drinking. In this case we are interested in determining if the wearer has taken excessive amounts of alcohol and thus would look for inferences of this from other the other sensors.

The GPS sensor can be linked to a map containing all known bars. Alternatively, the normal motion of the wearer when walking can be compared with the current motion and their degree of inebriation inferred from it. Increased side to side motions can be taken as indicative of inebriation.

It is to be appreciated that the provision of a GPS receiver is not limited to the embodiment of an anklet. It may also be provided as part of any other wearable device used as part of the system, or as part of a portable computing device such as a smart phone which can form part of a system according to the disclosure. In all cases, an additional function could be the inference of drunk driving, when a GPS receiver provides inference of a drunken walk and then rapid motion representing being in a vehicle, in combination with motion sensor information that corresponds to steering or other driving motions.

Figure 7:
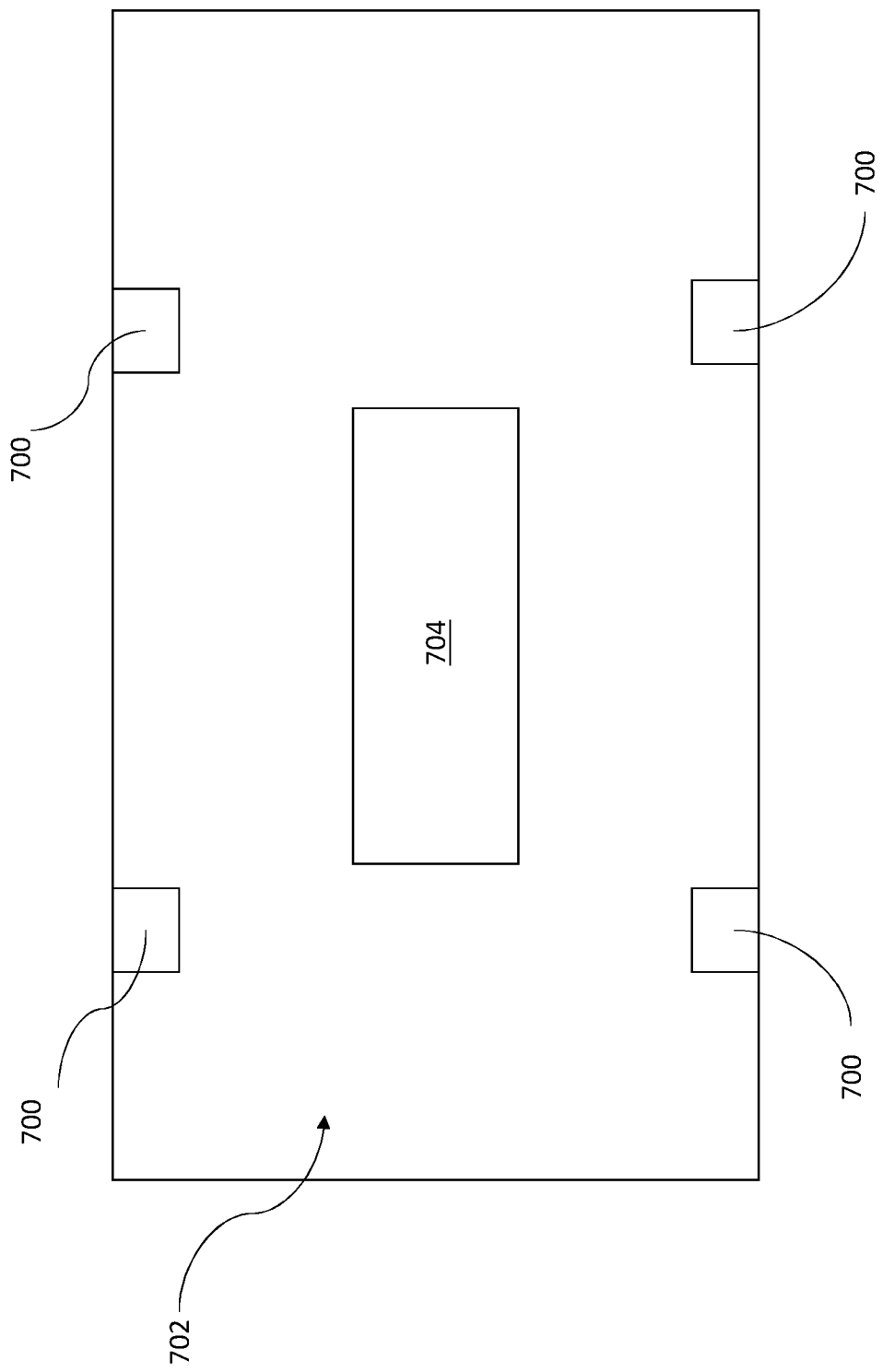
FIG. 7 shows a fifth embodiment of an ingestion detection system, showing a plan view of a room where a plurality of fixed position acoustic transducers are provided.

FIG. 7 illustrates a fifth embodiment, showing a plan view of a room 702 where a plurality of fixed position acoustic transducers 700 are provided. Here a plurality of sensors are shown but the system could equally be implemented with a single sensor. They may be positioned at selected points around a dining table 704. The acoustic detection and circuit set up of this embodiment may be similar to those set out in previous embodiments, but instead is housed remotely from the user. Here the fixed position acoustic transducers 700 may be placed in an electric socket mounted device, on (or in) a fridge, at a cooker, or in a wall plug powered unit. The functionality of the system may also be combined with that for another device such as a charger, data signal relay device, or wireless hub. The fixed position acoustic transducers 700 may be wall or ceiling mounted; be provided as standalone devices that can sit on a shelf or worktop, or be provided in the floor.

The fixed position acoustic transducers 700 are intended to be placed in the dining or kitchen area, and will listen for sounds related to food consumption.

There is the possibility to identify the eater through looking at the proximity of their mobile device to the acoustic transducers (for example by received radiofrequency signal strength indication (RSSI), bluetooth or equivalent methods), other wearable device or through looking for specific personal acoustic patterns associated with that eater. If necessary a plurality of microphones can be used to allow triangulation of sounds and/or radio frequency signals. If the plurality of microphone receivers is dispersed outside a single unit there will be a need to calibrate the relative distances between them. This can be done by each device in turn simultaneously sending a radio signal and a known acoustic pulse. The other receiver units will detect the acoustic pulse and report its arrival to the master unit allowing initial inter-receiver distances to be calculated.

Figure 8:
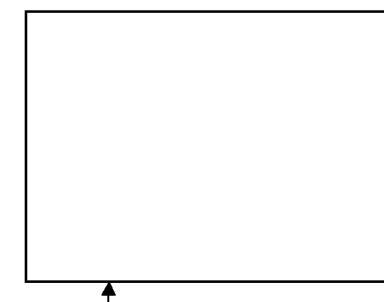
FIG. 8 shows a sixth embodiment of an ingestion detection system, embodied in a mobile device.
Figure 8:

FIG. 8 illustrates a sixth embodiment, where the ingestion monitoring functionality is embedded with in a mobile device 800. The mobile device's microphone and acoustic path and audio circuits can be customised to allow the required acoustic functionality. The low frequency response of microphones and the following filters for telephony are generally clipped to remove low frequency sounds, partly to aid compression of voice data and partly to remove unwanted sounds such as those generated by wind. To this end it is envisaged that filtering of the acoustic signal for voice is moved more into the digital domain to allow low frequency sound and infra-sound to be available for our purpose.

As mobile devices are generally held close to the user, a proximity test can provide a way of identifying the specific user in cases where the user is not alone.

The disclosure may also provide means to provide various alerts to a user once an ingestion event is detected. Also, the disclosure may provide means to record a log of ingestion and other events, which may be presented to a user for their information.

In one aspect, where a wearable device or portable computing device is provided, the detection of an ingestion event can cause the device to generate an audible and/or visual alarm. Suitable loudspeaker or display apparatus can be provided at the wearable device or portable computing device for this purpose (and existing hardware can be used under the control of a suitable application or firmware).

In embodiments where a remote server is used for performing signature identification or other tasks, it may send a command back to the wearable device or portable computing device for the generation of an alarm. However it may in addition or instead take other action, such as sending a text message or an e-mail.

Ingestion data may also be provided to the user, by logging on to a website or by means of an application run on a portable computing device. The data can be used to identify trends, set goals and provide motivational encouragement or practical advice for modifying food consumption or altering lifestyle choices.

Various modifications and improvements can be made to the above without departing from the scope of the disclosure.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

The method as described above may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multi-chip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

The invention claimed is:

1. An ingestion monitoring system comprising:
  a wristband attachable on a wrist of a user, the wristband comprising
    a housing,
    a first acoustic transducer mounted on the housing so as to face the wrist to sense vibrations transmitted through the body of the user,
    a second acoustic transducer mounted on the housing so as to be isolated from the wrist to sense airborne sounds,
  a motion sensor, a heart rate monitor, a photoplethysmographic sensor and an analogue to digital converter arranged to convert electrical signals from the acoustic transducers, the motion sensor, the heart rate monitor and the photoplethysmographic sensor to digital signals; and
  a processor arranged to process the digital signals to detect an ingestion event, wherein the processor is adapted to identify a movement of the user's arm detected by the motion sensor as a pattern which correlates with a given action, including cutlery use or eating by hand and physical exercise;
  wherein food or drink consumption is inferred when there is an increase in heart rate and blood profusion in subcutaneous blood vessels without a corresponding motion of the arm that correlates to exercise.

2. The system of claim 1, further comprising one or more other types of sensors which provide ancillary data for correlation with acoustic signals, wherein one sample from each of the sensor types is considered as a vector and an event is a time evolution of that vector.

3. The system of claim 2, wherein raw signals generated by the sensors are transformed into a parameter space having a plurality of axis that coincide with indicators for given actions, wherein thresholding is applied directly to the indicators, whereby an action is deemed to have occurred when its threshold is exceeded.

4. The system of claim 2, comprising a signal classification model used to classify detected signals from the acoustic transducers and the said one or more other types of sensors wherein the signal classification model employs a Gaussian Mixture Model technique, a Hidden Markov Model technique, or a hybrid technique employing both Gaussian Mixture Model and Hidden Markov Model techniques.

5. The system of claim 1, wherein low frequency components are observed after low pass filtering and high frequency components are observed by transformation into a frequency domain over a sampling window.

6. The system of claim 1, wherein the processor is configured to execute a statistically derived model which assigns probable causes to signal events and over a series of events infers an activity that is taking place.

7. The system of claim 1, wherein the movement is classified as being vigorous, minimal, or still.

8. The system of claim 1, comprising a temperature sensor.

9. The system of claim 1, wherein the airborne sounds and the vibrations transmitted through the body of the user are correlated and combined to form part of a signature relating to an event.

10. The system of claim 1, comprising a portable computing device, and one or more fixed location acoustic transducers.

11. The system of claim 10 wherein the portable computing device comprises other types of sensors which provide ancillary data for correlation with acoustic signals.

12. The system of claim 10, wherein the computing device is adapted to identify sounds originating from one particular user based on the proximity of the portable computing device to one or more of the fixed location acoustic transducers.

13. The system of claim 1, wherein the wristband comprises a filter for filtering out high frequency noise prior to analogue to digital conversion and a communication circuitry for transmitting sensor data to a remote location for identification.

14. The system of claim 13, wherein the processor is comprised in a remote server and wherein the server is configured to run a statistically derived model or signal classification model.

15. The system of claim 1, wherein the processor is comprised in the wristband.

16. The system of claim 1, wherein the photoplethysmographic sensor is arranged to detect a period of apnoea related to a swallowing event, wherein a swallowing event is detected when a period of apnoea is correlated with an acoustic swallowing signature from airborne or intra-body vibrations.

17. A method of monitoring ingestion, comprising
  providing a wristband attachable on a wrist of a user, the wristband comprising a housing, a first acoustic transducer mounted on the housing so as to face the wrist to sense vibrations transmitted through the body of the user and a second acoustic transducer mounted on the housing so as to be isolated from the wrist to sense airborne sounds, a motion sensor, a heart rate monitor, a photoplethysmographic sensor and an analogue to digital converter;

converting analogue electrical signals from the acoustic transducers, the motion sensor, the heart rate monitor and the photoplethysmographic sensor to digital signals;

providing a processor;

processing the digital signals to detect an ingestion event, wherein the processor is adapted to identify a movement of the user's arm detected by the motion sensor as a pattern which correlates with a given action, including cutlery use or eating by hand and physical exercise; and inferring food or drink consumption when there is an increase in heart rate and blood profusion in subcutaneous blood vessels without a corresponding motion of the arm that correlates to exercise.

18. A wristband attachable on a wrist of a user, the wristband comprising a housing, a first acoustic transducer mounted on the housing so as to face the wrist to sense vibrations transmitted through the body of the user and a second acoustic transducer mounted on the housing so as to be isolated from the wrist to sense airborne sounds, a motion sensor, a heart rate monitor, a photoplethysmographic sensor, an analogue to digital converter arranged to convert electrical signals from the acoustic transducers, the motion sensor, the heart rate monitor and the a photoplethysmographic sensor to digital signals, and a communication circuitry for sending the digital signals to a remote location for processing to detect an ingestion event, to identify a movement of the user's arm detected by the motion sensor as a pattern which correlates with a given action, including cutlery use or eating by hand and physical exercise, and to infer food or drink consumption when there is an increase in heart rate and blood profusion in subcutaneous blood vessels without a corresponding motion of the arm that correlates to exercise.

* * * * *